(12) United States Patent
Mirizzi et al.

(10) Patent No.: US 7,163,546 B2
(45) Date of Patent: Jan. 16, 2007

(54) METHOD AND APPARATUS FOR AVULSION OF VARICOSE VEINS

(76) Inventors: Michael S. Mirizzi, 6509 Pajaro Ct., San Jose, CA (US) 95120; Mark P. Parker, 5569 Dent Ave., San Jose, CA (US) 95118; Radit Tantisira, 2779 Barclay Way, Ann Arbor, MI (US) 48105; John Rodriguez, 3900 Moorpark Ave., #148, San Jose, CA (US) 95117

( * ) Notice: Subject to any disclaimer, the term of this patent is extended or adjusted under 35 U.S.C. 154(b) by 64 days.

(21) Appl. No.: 10/309,940

(22) Filed: Dec. 3, 2002

(65) Prior Publication Data

US 2003/0125759 A1    Jul. 3, 2003

Related U.S. Application Data

(60) Provisional application No. 60/342,719, filed on Dec. 21, 2001.

(51) Int. Cl.
*A61B 17/32* (2006.01)

(52) U.S. Cl. .................................... 606/159

(58) Field of Classification Search ............. 606/157, 606/158, 159, 170, 167; 600/36
See application file for complete search history.

(56) References Cited

U.S. PATENT DOCUMENTS

| | | | |
|---|---|---|---|
| 3,508,553 A | | 4/1970 | Kanbar et al. |
| 3,568,677 A | | 3/1971 | Nolan et al. |
| 3,764,427 A | | 10/1973 | Reimels |
| 3,764,437 A | | 10/1973 | Reimels |
| 4,517,965 A | | 5/1985 | Ellison |
| 5,011,489 A | | 4/1991 | Salem |
| 5,792,168 A | | 8/1998 | Suval |
| 5,843,104 A | * | 12/1998 | Samuels ............ 606/159 |
| 5,893,858 A | | 4/1999 | Spitz |
| 6,019,771 A | * | 2/2000 | Bennett et al. ......... 606/159 |
| 6,030,200 A | | 2/2000 | Samuels |
| 6,042,538 A | * | 3/2000 | Puskas ............... 600/114 |
| 6,071,292 A | * | 6/2000 | Makower et al. ........ 606/158 |

(Continued)

FOREIGN PATENT DOCUMENTS

WO    WO 94/21177 A1    9/1994

(Continued)

OTHER PUBLICATIONS

Ricci, Stefano. et al., *Ambulatory Phlebectomy: A Practical Guide for Treating Vericose Veins*. Mosby—Yearbook, St. Louis, MO., (1995) pp. 67-167.

(Continued)

*Primary Examiner*—Anhtuan T. Nguyen
*Assistant Examiner*—Elizabeth Houston
(74) *Attorney, Agent, or Firm*—Knobbe, Martens, Olson & Bear, LLP (57) ABSTRACT

Apparatuses and methods for removing veins, usually varicose veins, rely on endoluminal capture of a distal end of the vein segment to be removed. In the illustrated embodiments, a shaft having reciprocatable penetrating elements is used to engage and capture the distal end of the vein. After rotating the shaft to pull the distal segment of the vein away from the connecting tissue, the shaft is withdrawn proximally, invaginating the segment back to the point of insertion.

11 Claims, 9 Drawing Sheets

U.S. PATENT DOCUMENTS

| | | | |
|---|---|---|---|
| 6,077,261 A * | 6/2000 | Behl et al. | 606/50 |
| 6,077,289 A | 6/2000 | Mollenauer | |
| 6,652,549 B1 * | 11/2003 | Welten | 606/159 |
| 6,887,251 B1 * | 5/2005 | Suval | 606/159 |
| 2003/0225426 A1 * | 12/2003 | Hill et al. | 606/159 |
| 2004/0087367 A1 * | 5/2004 | Hendrickson | 463/42 |

FOREIGN PATENT DOCUMENTS

| | | | |
|---|---|---|---|
| WO | WO 99/17664 A1 | 4/1999 | |
| WO | WO 00/42918 | * | 7/2000 |
| WO | WO 00/45691 A2 | 8/2000 | |
| WO | WO 01/37739 A1 | 5/2001 | |

OTHER PUBLICATIONS

Weiss, Robert A., et al., Eds., *Vein Diagnosis and Treatment: A Comprehensive Approach*.McGraw Hill Medical Publishing Division, New York, (2001) Chapter 22, pp. 197-210.

* cited by examiner

METHOD AND APPARATUS FOR AVULSION OF VARICOSE VEINS

CROSS-REFERENCES TO RELATED APPLICATIONS

The present application claims the benefit of U.S. Provisional Patent Application Serial No. 60/342,719, filed Dec. 21, 2001, the full disclosure of which is incorporated herein by reference.

BACKGROUND OF THE INVENTION

The present invention relates generally to medical devices and methods. More particularly, the present invention relates to methods and apparatus for removing veins from surrounding connective tissue.

Various techniques have been developed to treat varicose veins. In simple cases, elevation of the legs and compression stockings may be sufficient therapy to mitigate the progression of the varicose veins. An alternative therapy includes "sclerotherapy." In the procedure, the diseased veins are injected with a sclerosing solution, such as sodium tetradecyl sulfate, along the tract of the varicose vein. Typically, multiple injections are administered during a treatment session. The sclerosing solution causes subsequent inflammation and damage to the endothelial cell lining of the vein. This damage and contraction in conjunction with post-procedural external compression results in localized occlusion or contraction of the vessel which forces rerouting of the blood through other conduits and in ideal circumstances causes the vein to become a fibrin cord which is resorbed over time. With this therapy, patients typically require two or more treatment sessions in order to satisfactorily alleviate the varicose veins. However, typically the technique does not provide a permanent or complete solution with varicose veins reoccurring over time. Consequently, sclerotherapy is often combined with a more invasive operation such as ligation and/or stripping of the saphenous vein. In additionally, sclerotherapy is not without the potential for complication. These can include the potential for browning splotches or bruising of the skin, formation of blood clots in the veins, inflammation, adverse allergic reactions, ulceration, phlebitis, anaphylactic overdose, ischemia, skin or fat necrosis, and peripheral neuropathy.

In another technique, varicose veins are removed by "stab-avulsion phlebectomy" with small surgical hooks. In this technique, the varicose veins are removed and/or ligated through a series of separate small skin incisions. These incisions are made along the vein path and the vessel is exteriorized using small hooks and forceps. Once exteriorized, the loop is put under traction, divided, and both ends avulsed separately. When a loop of a larger varicose vein is exteriorized, it is pulled with rocking motions. These alternating traction movements permit detachment from perivenous tissue as well as allow for further identification of the vein path. During this procedure compression is applied at the incision locations to promote hemostasis. With this therapy patients typically only require one treatment session. However, in many cases dependent on the skill of the surgeon and on the extent of the varicose anatomy, the procedures is very time intensive and can take between 2–3 hours to complete. In addition, the procedure also requires multiple incisions and in many cases the veins tend to fragment into small segments while being avulsed making it difficult to entirely remove the targeted veins. Finally, patients typically experience ecchymosis (bruising) for up to four weeks post-operatively and in more extreme instances can experience complications including infection, deep or superficial thrombophlebitis, lymphorrhea, paresthesia and hematoma.

In addition to these procedures which are in clinical use, it has been proposed in the patent and medical literature to use intravenous devices for invaginating and stripping vericose veins. For example, U.S. Pat. No. 6,030,396, describes a device which is introduced through a venous penetration and advanced to a distal location within the venous lumen. The lumen is surgically opened at the distal location and the vein severed. The severed end of the vein is then sutured to the device, and the device withdrawn proximally to evert and remove the vein. Although a promising procedure, the need to surgically open the proximal venous location and suture the vein to the device is a drawback of the procedure. An analogous procedure for removing varicose veins using an endoscope is described in published PCT Application WO 00/45691. In that patent application, an endoscope having several channels is introduced through a penetration into the venous lumen, preferably over a guidewire. While visualizing the luminal wall, a balloon is inflated and facilitates frictional engagement of the vein segment prior to removal. WO 94/21177 describes use of a device with exposed barbs for endoluminal introduction and capture of a vein prior to avulsion and removal.

In view of the above, it would be desirable to provide improved apparatus and methods for venous removal, particularly for the removal of vericose veins in a minimally invasive. It would be particularly useful to provide apparatus and methods which may be performed endovascularly, i.e., through the venous lumen and which simplify capture and retraction of a distal end of the vein to remove, and optionally without the need for visualization, particularly endoscopic visualization, during the procedure. Such procedures should preferably require only a single tissue penetration to permit introduction of the removal apparatus, while providing for simplified and improved methods for capturing and avulsing a distal end of the vein remote from the introductory point. At least some of these objectives will be met by the inventions described hereinafter.

Relevant U.S. Patents include U.S. Pat. Nos. 6,077,289; 6,030,396; 5,893,858; 5,011,489; 4,517,965; 3,764,427; 3,568,677; and 3,508,553. Relevant PCT Publications include WO 01/37739; WO 00/45691; WO 99/17664; and WO 94/21177. Descriptions of phlebectomy and related procedures are found in *Ambulatory Phlebectomy*, Ricci and Georgiev with Goldman, pp 67–126 Mosby—Year book, Inc., St. Louis, Mo. and *Vein Diagnosis and Treatment: A Comprehensive Approach*, Weiss et al. Eds., McGraw Hill Medical Publishing Division, New York 2001, Chapter 22, pp 197-210.

BRIEF SUMMARY OF THE INVENTION

The methods and apparatus of the present invention permit the endoluminal removal of blood vessels, usually veins, and more usually varicose veins. By "endoluminal" it is meant that the removal device is introduced into the venous lumen and manipulation of the removal device accomplishes detachment of the vessel wall from the surrounding connecting tissue and removal of the separated vessel wall through a tissue penetration that has been made to introduce the removal device. Penetration can be made through a small incision and venotomy, or through a less invasive percutaneous approach where an introductory sheath is introduced through the tissue into the vein. Optionally, after being accessed, the proximal end of the vein can be severed and removed through the access incision to provide for vein exteriorization. The removal device of the present invention can then be introduced through the free end of the vein which has been exteriorized. The methods of the present invention will typically be used for removing varicose or other damaged veins.

Methods according to the present invention for removing a vein or other blood vessel having a vessel wall from tissue comprise introducing a shaft of the removal device through a tissue penetration and into a lumen of the vein at a proximal location. A distal end of the shaft typically has fully retracted penetration element(s) and is advanced in a distal direction through the lumen to a distal location. References to "proximal" and "distal" refer to the position relative to the initial venous access point. The initial access point will be considered the proximal location while the remote target site at which the vein is first captured and detached from the surrounding connective tissue is the distal location. Generally, the shaft may be advanced in either a prograde (i.e., in the direction of blood flow) or retrograde (i.e., opposite to the direction of blood flow) direction. Usually, however, the shaft will be advanced in the prograde direction since it will pass more easily through the venous valves.

The proximal location and the distal location represent the terminal ends of the vein segment which is desired to be removed. The penetrating element(s) is (are) advanced from the shaft and exposed so that the vessel wall is captured with the penetrating element(s) at the distal location from within the lumen with the distal end of the shaft. After capturing the wall, and optionally severing or dissecting the vein at the proximal location, the shaft is manipulated to remove the vessel, usually by retracting the shaft in a proximal direction to avulse or invaginate the vessel wall from the tissue.

The shaft of the removal device may be manipulated in a variety of ways to remove the target length of vein or other blood vessel, either as a single piece or in a plurality of segments. Usually, the shaft will be initially rotated about its longitudinal axis in order to capture the end of the blood vessel and draw down the blood vessel onto the outside of the shaft. The shaft may then be withdrawn proximally in order to avulse the blood vessel to be removed, or at least a portion or segment thereof. If only a portion or segment of the target blood vessel length is removed, the procedure may be repeated. Alternatively, the shaft of the removal device may be rotated an amount sufficient to draw down at least one-half of the length of the blood vessel to be removed, sometimes drawing down the entire length of the blood vessel to be removed. In the latter case, the blood vessel may be removed with little or substantially no avulsion. In all these cases, if less than the target length of blood vessel has been removed, the removal steps may be repeated in order to remove the remaining length or segments of the blood vessel.

Optionally, the vessel wall may be captured without having to form any external tissue penetrations in the region of the distal location. Alternatively, however, a percutaneous or open surgical incision could be made near the distal location in order to sever the distal end of the vein segment to be removed. As a still further alternative, the vessel wall could be severed at or near the distal location in an endoluminal manner, i.e., using a tool which has been endoluminally introduced to the distal location, for example using a blade or other severing instrument which is present on the removal device itself.

Capturing the distal end of the vein segment to be removed typically comprises engaging at least one penetrating element from the shaft of the removal device into the vessel wall to permit manipulation thereof. Preferably, the shaft is then rotated and/or axially retracted in order to separate the vessel wall from the surrounding connecting tissue at that location. The shaft is then proximally retracted in order to complete avulsing the vessel wall to separate the wall from connecting tissue and remove the wall through the proximal tissue penetration. Usually, the removed venous segment will be severed or torn from the remaining portion of the vessel wall after the shaft has been retracted back through the tissue penetration at the proximal wall location.

Optionally, a signal may be emitted from the distal end shaft prior to capturing the distal end of the vessel segment to be removed. By observing the position of the signal, which is usually a visible light signal, the position of the removal device can be tracked to determine when the distal end of the shaft has reached the distal location of the venous lumen which is within the venous segment to be removed. Usually, multiple venous segments will be removed sequentially, and availability of the light or other signal allows the physician to mark the patient's skin at the distal location which then becomes the proximal access point for the next avulsion step.

In addition to these methods, the present invention provides apparatus for removing a vein segment from tissue. The apparatus comprises a shaft having a proximal end and a distal end. A mechanism is disposed at or near the distal end of the shaft for endoluminally penetrating a venous wall to a depth selected to capture the wall and permit separation of the wall from underlying connective tissue. A handle is disposed at the proximal end of the shaft and includes an actuator coupled to the penetrating mechanism so that the user may selectively actuate and engage the distal end of the venous segment when it has been properly located. The shaft may be rigid or may be flexible to facilitate introduction through the venous lumen.

The penetrating mechanism will include at least one penetrating element which is reciprocatably attached to the shaft to shift between a fully retracted position and a radially extended position. Usually, at least two such penetrating elements will be provided, and three, four, or even more may be provided in certain instances. The penetrating elements may be resilient or malleable and will be deployable to protrude from the shaft in a radial direction (or at least a direction having a significant radial component) such that the distance of the distal tip of the penetrating element from the surface of the shaft will be in the range from 0.25 mm to 10 mm when fully extended, preferably being in the range from 0.5 mm to 1.5 mm when fully extended. The resilient penetrating elements will be preshaped to deflect outwardly as they are advanced. In contrast, the soft or malleable element will typically be formed in situ as they are advanced over a ramp or cam which deflects them outwardly. The penetrating elements will typically have a maximum width in the range from 0.1 mm to 2 mm, usually from 0.25 mm to 1 mm. In the case of penetrating elements having circular geometries, the width will of course be a diameter. The length of the penetrating elements 20 is less critical and will depend largely on the extent to which the elements extend proximally into the shaft. The length and diameter of the shaft will vary depending on the nature of the target needed to be removed. For typical varicose veins, the shaft will have a length in the range from 5 cm to 40 cm, preferably from 10 cm to 20 cm, and a maximum width, typically a diameter for circular shafts, in the range from 1 mm to 6 mm, preferably from 1 mm to 2 mm.

In the exemplary embodiments, the penetrating elements are inclined at an angle relative to the axis of the shaft when radially extended from the shaft. Typically, the penetrating elements are disposed distally and inclined at an angle in the range from 5° to 80° relative to the shaft axis, usually from 5° to 60° relative to the shaft axis when radially extended. Alternatively, the penetrating element(s) may be proximally disposed and at an inclined angle when radially extended. Such proximally inclined penetrating elements will be disposed at an angle relative to the axis of the shaft in the range from 5° to 80°, usually from 5° to 60°. The invention, however, is not limited to inclined penetrating elements and in some instances elements which are disposed at 90° relative to the shaft axis will also find use.

In preferred aspects, the apparatus of the present invention may comprise a signal generating element disposed near the distal end of the shaft. The signal generating element will be selected to provide an observable signal external to the patient and indicative of the position of the distal end of the shaft. Conveniently, the signal generating element can be a visible or infrared light source which can be visually tracked or tracked using appropriate detectors, on the skin of the patient.

DETAILED DESCRIPTION OF THE INVENTION

Figure 1:
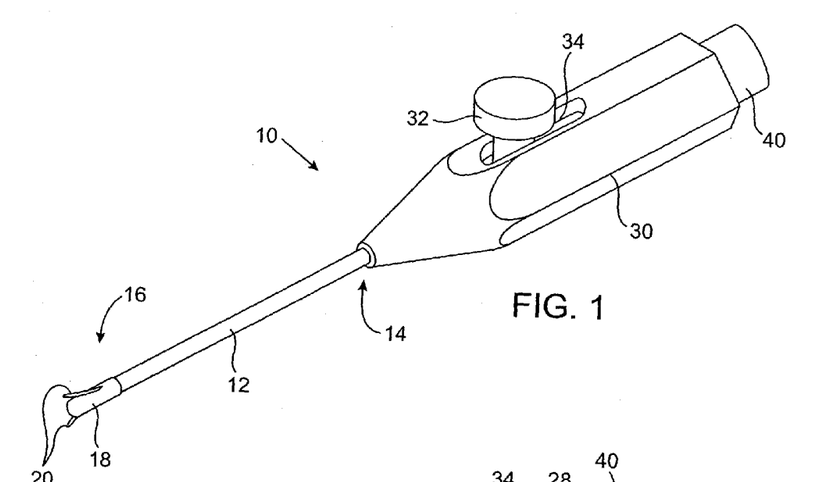
FIG. 1 is a perspective view of an apparatus for removing a vein from tissue constructed in accordance with the principles of the present invention.
Figure 2:
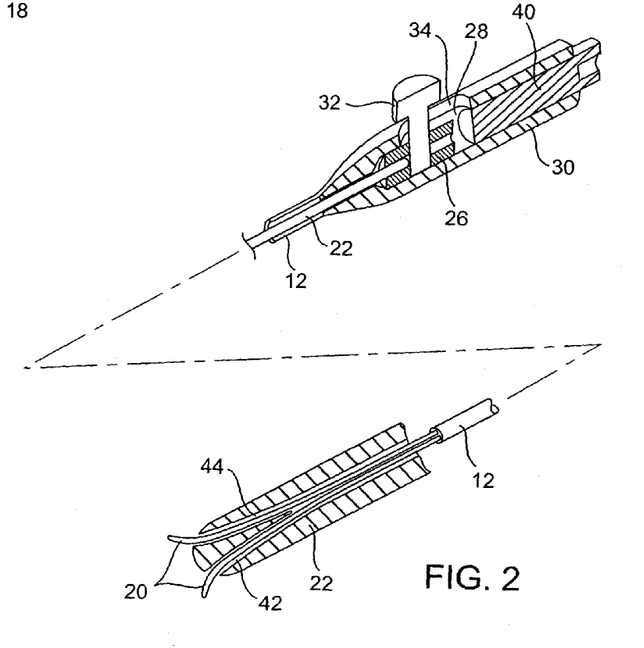
FIG. 2 is a cross-sectional view of the apparatus of FIG. 1, with the distal tip enlarged relative to the rest of the device.

Referring now to FIGS. 1 and 2, a vein removal apparatus 10 constructed in accordance with the principles of the present invention includes a shaft 12 having a proximal end 14 and a distal end 16. The shaft 12 terminates in a blunt bullet tip 18 through which a pair of penetrating elements 20 may be deployed by selectively advancing and retracting the elements relative to the apparatus. As will be described in greater below, advancing the penetrating elements 20 causes them both to move forwardly or distally relative to the device and to simultaneously move radially outwardly. The penetrating elements 20 are shown in their deployed configurations in FIGS. 1 and 2. A pushrod (or pushtube) 22 is disposed within a central lumen or passage of the shaft 12 and is connected at its distal end to the proximal ends of the penetrating elements 20. A proximal end of the shaft 22 is connected to a sliding block 26 which is received in a central passage 28 of handle 30. A thumb slide 32 is connected to the sliding block 26 and is received in a slot 34 formed in the handle 30. In this way, a user may selectively advance and retract the penetrating elements 20 by manually advancing and retracting the thumb slide 32. The handle 30 further includes an end plug 40 which closes its proximal end. Of course, the need to provide a pushrod or pushtube 22 can be obviated by extending proximal ends of the penetrating elements 42 and 44 rearwardly so that they are received directly in the sliding block 26. Other mechanical variations may also be employed. For example, an O-ring may be situated in the shaft passage about the pushrod 22 in order to isolate the handle from blood and other contamination.

The shaft 12 may be rigid, semi-rigid, or flexible. Rigid structures may be formed from stainless steel. Semi-rigid and flexible structures may be formed from shape memory alloys, such as nickel-titanium alloy, reinforced polymeric materials, close wound coils, or may be formed as gooseneck or other conventional shapeable shaft structures. The length and width (usually diameter) of the shaft will be selected to accommodate the target vein segment to be removed. Exemplary lengths and widths are set forth above.

The bullet tip 18 is attached to the distal end of the shaft 12 by conventional techniques and will usually include at least one passage therethrough for deployment of at least one penetrating element. As illustrated in FIGS. 1 and 2, the bullet 18 includes a pair of diverging passages 42 and 44 which outwardly deflect the penetrating elements 20, as illustrated. A greater or lesser number passages may be provided, depending on the number of penetrating elements utilized.

Figure 3A:
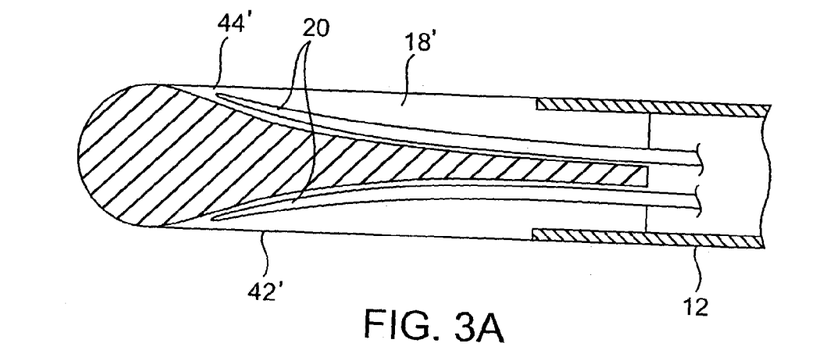
FIGS. 3A and 3B are further enlarged cross-sectional illustrations of the distal tip of the apparatus of FIG. 1.
Figure 3B:
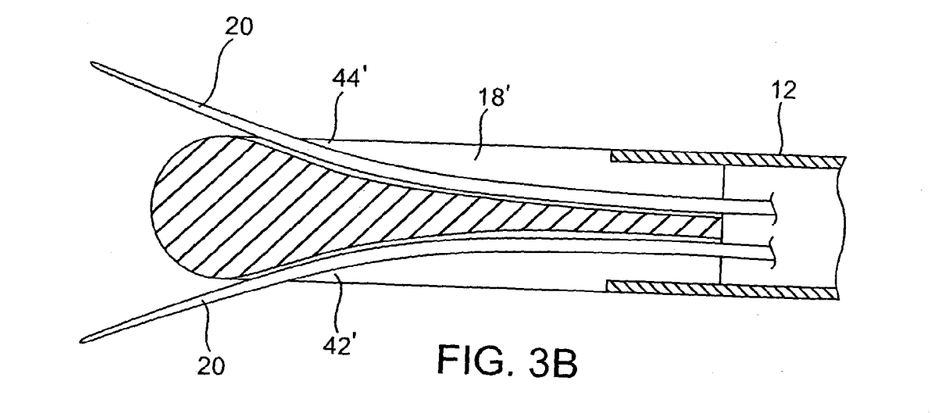
Figure 3C:
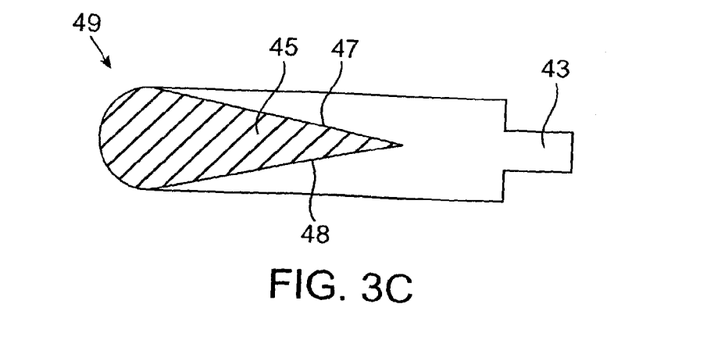
FIG. 3C is an alternative distal tip configuration shown in cross-section.
Figure 4A:
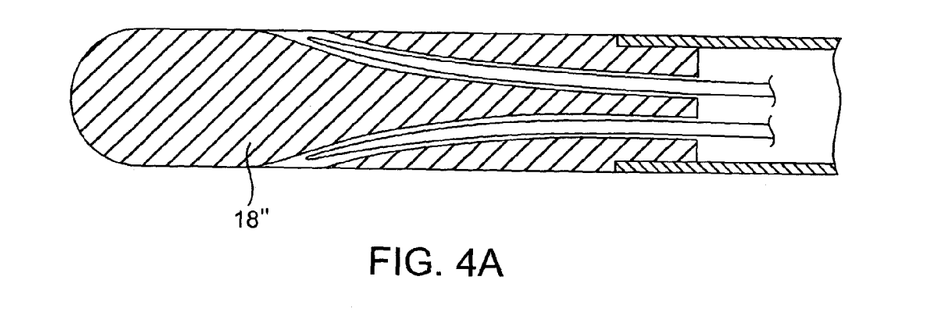
FIGS. 4A and 4B are similar to FIGS. 3A and 3B, except that the deployment channels for the tissue penetrating elements are closed and inclined at a greater angle relative to the axis of the device. This results in the penetrating elements extending a greater radial distance from the device, but a shorter axial distance from their point of emergence.
Figure 4B:
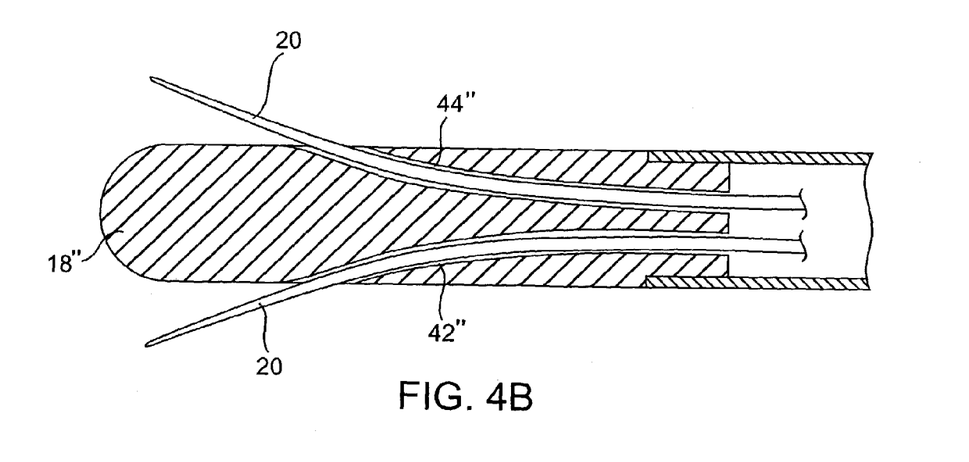

The geometry of the bullet tip and penetrating element deployment passages may be selected to deploy the penetrating elements in a desired pattern. For example, FIGS. 3A and 3B, bullet tip 18' has a pair of open channel deployment passages 42' and 44' which cause penetrating elements 20 to deploy radially outwardly and forwardly of the distal end of the bullet 18' as shown in FIG. 3B. Alternatively, as shown in FIGS. 4A and 4B, bullet tips 18" have closed channel deployment passages 42" and 44" which direct the penetrating elements 20 at a sharper angle away from the emergent point within the tip. Thus, the penetrating elements 20 will advance a greater radial distance from the bullet tip, but will not advance as far in the distal direction. By properly selecting the mechanical nature of the penetrating elements (as discussed in more detail below) and the geometry of the deployment channels, a wide variety of deployment geometries can be effected. FIG. 3C illustrates yet another embodiment where a triangular ramp 45 defines diverging surfaces 47 and 48 in bullet tip 49. In all cases, the bullet tips 18 and 49 are attached to the open distal end of shaft 12 by securing a projection 43, as illustrated in FIG. 3C.

Figure 5A:
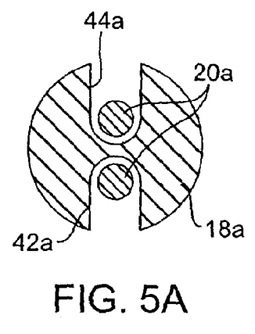
FIGS. 5A–5C illustrate alternative cross-sectional shapes for the penetrating element channels formed within the apparatus of FIG. 1.
Figure 5B:
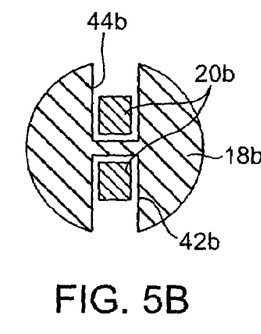
Figure 5C:
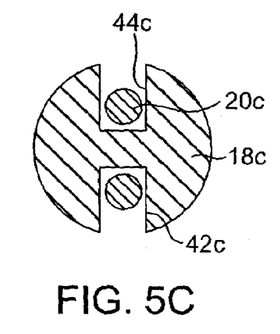

Referring now to FIGS. 5A–5C, the penetrating elements 20 may have a wide variety of configurations and be composed of a wide variety of materials. For example, penetrating elements 20a have a circular cross-section and are received in U-shaped passages 42a and 44a in bullet tip 18a. While penetrating elements having circular cross-sections will be the most common, penetrating elements 20b having square cross-sections are illustrated in FIG. 5B. Exemplary dimensions have been described above. Channels 42b and 44b are shown to have rectangular cross-sections, restricting torsion of the penetrating elements 20b. Restriction of torsion can limit lateral deflection of the penetrating elements 20b, if desired. In some instances, however, it will be preferred to have the cross-section of the penetrating element to be mismatched with the cross-section of the deployment channel. As shown in FIG. 5C, circular penetrating elements 20c are received in rectangular deployment channels 42c and 44c. Such an arrangement is advantageous in that it reduces friction during deployment. A wide variety of other combinations and cross-sections, both matched and mismatched, may be employed within the scope of the present invention.

For distally extending penetrating elements 20, as illustrated in FIGS. 1–4, the penetrating elements 20 will be inclined at a distally forward angle in the range from 5° to 80°, usually from 5° to 60°. Penetrating elements will typically be composed of stainless steel, but could also be composed of shape memory alloys, such as a nickel titanium alloy, as well as resilient plastics. Usually, penetrating elements will be resilient so that they spring outwardly as they are advanced from the apparatus. Alternatively, the penetrating elements could be formed from a malleable metal which is deformed to bend at a desired angle as it extends outwardly from the vein removal apparatus.

Figure 6:
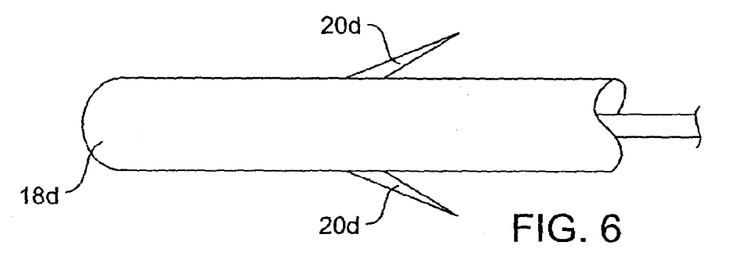
FIG. 6 illustrates an alternative penetrating element deployment geometry, with the penetrating elements inclined in a proximal direction.
Figure 7:
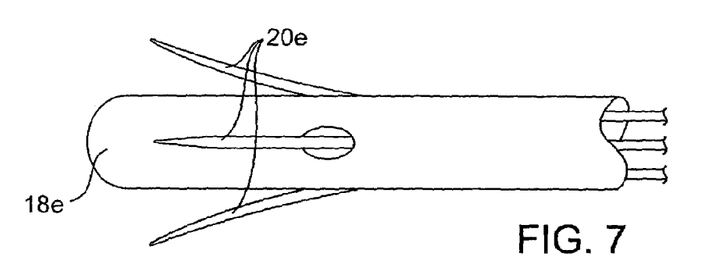
FIG. 7 illustrates another alternative configuration for the penetrating elements of the present invention, shown with four penetrating elements extending in a distal direction from their points of emergent.

Numerous other designs and configurations for the penetrating elements of the present invention will also be possible. Referring to FIG. 6, a pair of reciprocatable penetrating elements 20d are mounted in a bullet tip 18d so that they emerge in a proximal direction and can be penetrated into tissues by drawing the associated device in a proximal direction. Referring to FIG. 7, fewer or more than two penetrating elements can be provided. In the embodiment of FIG. 7, four penetrating elements 20e are reciprocatably mounted in a bullet tip 18e. Other embodiments having only a single penetrating element and/or having five or more penetrating elements will also be within the scope of the present invention.

Figure 8:
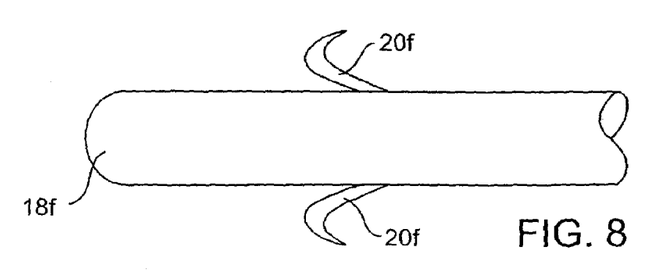
FIG. 8 illustrates yet another penetrating element configuration, with the penetrating elements shown to evert into a reward direction relative to the shaft of the device.

Referring to FIG. 8, a pair of penetrating elements 20f are reciprocatably mounted in a bullet tip 18f. The penetrating elements 20f are however resilient and possess a natural shape of an everting curve. Thus, as penetrating elements 20f are extended radially from the bullet tip 18f, they first emerge in a generally distal direction. As they are further advanced, the sharpened tips turn rearwardly so that they reach the fully everted configuration shown in FIG. 8.

Figure 9:
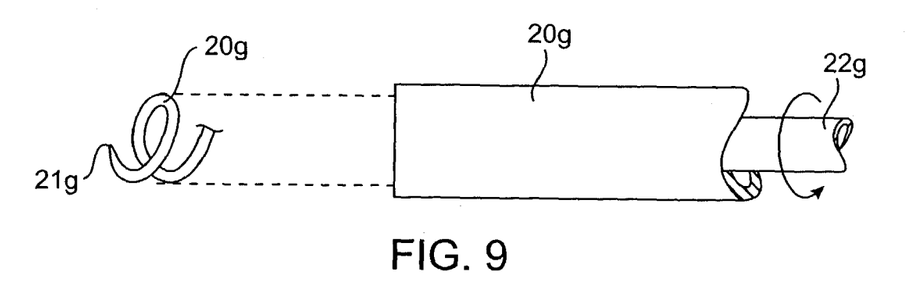
FIG. 9 illustrates a coil-shaped penetrating element according to the present invention.

Referring now to FIG. 9, a helical penetrating element 20g can be advanced distally from the distal end of a distal tip 20g. By rotating connecting shaft 22g, sharpened tip 21g of the helical penetrating element 20g can be cause to capture tissue. Optionally, the penetrating element 20g can then be withdrawn back into distal tip 20g to invaginate the vessel wall and facilitate removal.

Figure 10:
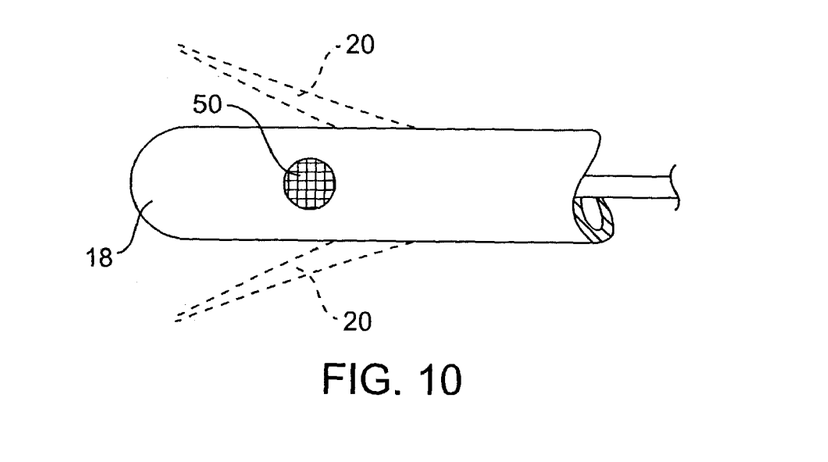
FIG. 10 illustrates a signal generator, in the form of a light source, disposed near the distal end of the apparatus of the present invention.

Referring now to FIG. 10, bullet tip 18 can be provided with a signal generating element 50, typically a visible or infrared light source. The signal generating element is useful for assisting in placement of the device, as described in more detail below.

Figure 11A:
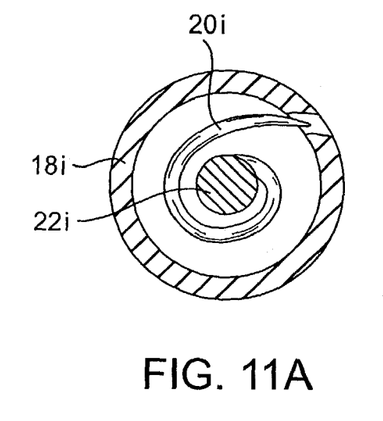
FIGS. 11A and 11B illustrate the radially deployment of a coiled penetrating element from a rotating shaft in the apparatus of the present invention.
Figure 11B:
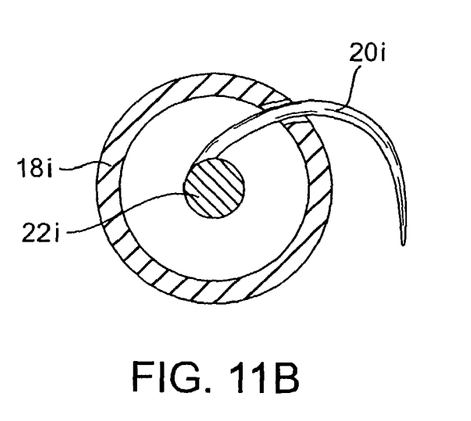

Referring now to FIGS. 11A and 11B, penetrating elements 20i can be provided as spiral structures wrapped around a rotatable deployment rod 22i in bullet tip 18i. By rotating the deployment rod 22i counterclockwise, (as observed in FIGS. 11A), penetrating element 20 will be withdrawn into the interior of the bullet tip 18i. By rotating deployment rod 22i in a clockwise direction, the penetrating element 20i will be advanced radially outwardly from the bullet tip 18i, as shown in FIG. 11B. Of course, spiral penetrating elements could be arranged to deploy by rotation in a counter-clockwise direction as well.

Figure 12A:
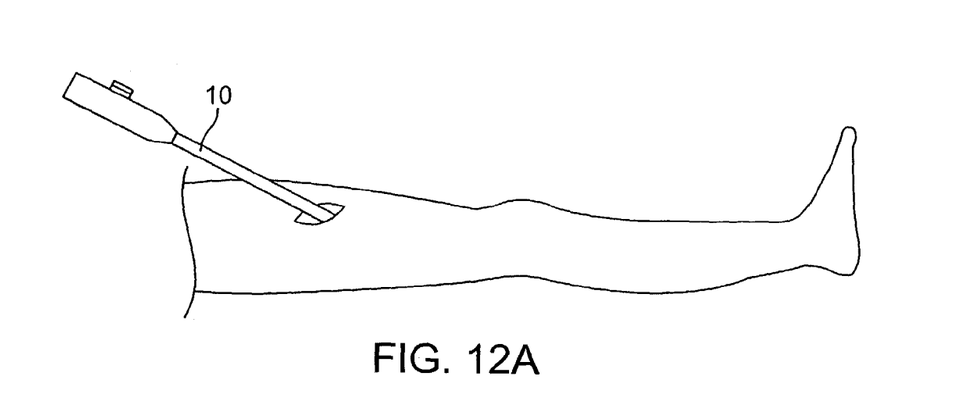
FIGS. 12A–12F illustrate use of the apparatus of FIG. 1 for removing a vein from the leg of a patient according to the method of the present invention.
Figure 12B:
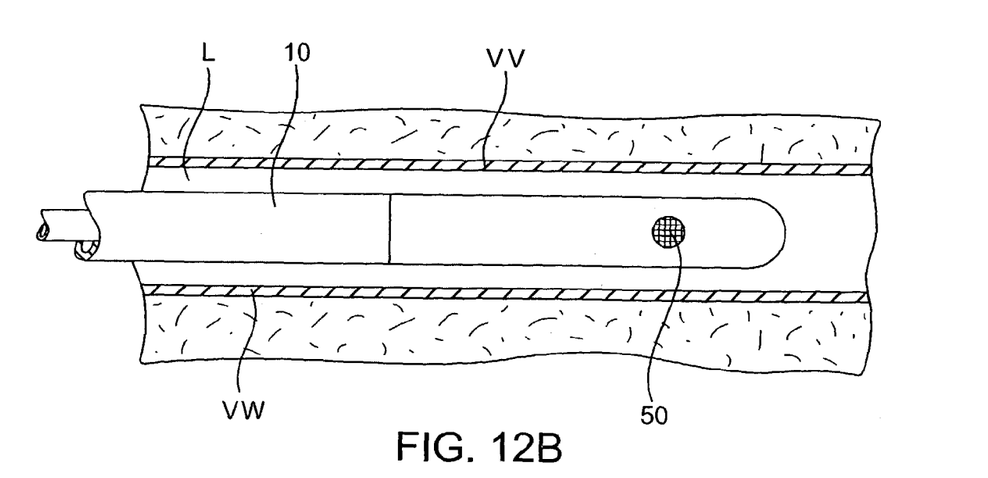

Referring now to FIGS. 12A–12F, removal of a varicose vein according to the method of the present invention will be described. As shown in FIG. 12A, a proximal end of a vein is exposed by a conventional surgical technique, such as a small incision, a small venotomy, vein exteriorization, or by another conventional percutaneous approach. The vein removal apparatus 10 is endoluminally introduced to the lumen (L) of the varicose vein (VV) to be removed, as shown in FIG. 12B. Optionally the light or other signal generating element 50 is used to correctly position the distal end of the device at the appropriate location.

As described thus far, the devices have employed resilient penetrating elements formed from a material having a good spring memory, such as spring stainless steel or a nickel-titanium alloy. It will also be possible to fabricate penetrating elements from a deformable or malleable material. Such deformable penetrating elements will be deflected and deformed as they are advanced over a ramp or other surface which changes their direction of travel.

Figure 11C:
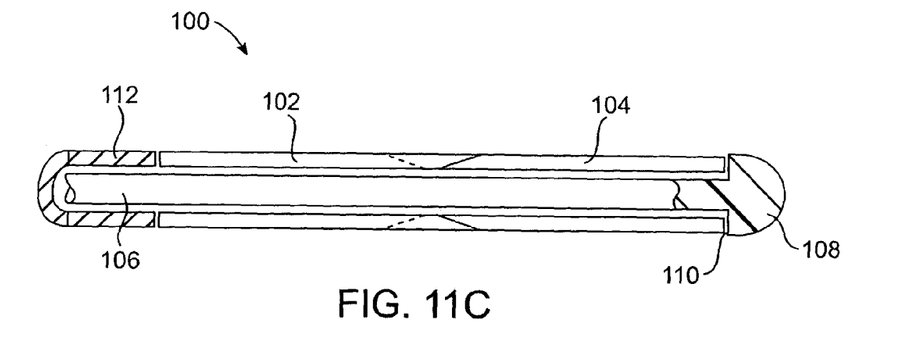
FIGS. 11C and 11D illustrate the deployment of deformable penetrating elements in both distal and proximal directions simultaneously.
Figure 11D:
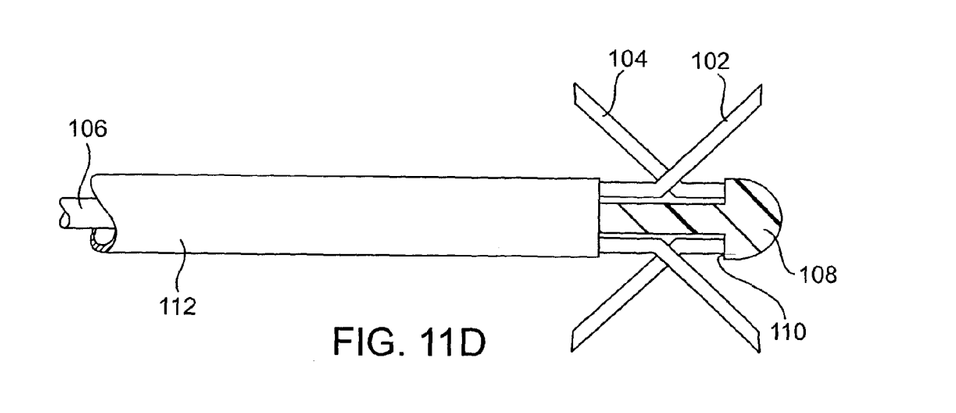

Also, as described thus far, the penetrating elements have been shown to advance in a single direction. It may sometimes be advantageous to employ multiple penetrating elements where different elements advance in different or opposite directions. For example, as shown in FIGS. 11C and 11D, a device 100 comprises a first set of distally disposed penetrating elements 102 and a second set of proximally disposed penetrating elements 104. The elements 102 and 104 are usually deformable or malleable so that they may be deflected in situ by advancement relative to a cam surface, as described below. The elements 102 and 104 are mounted on a shaft 106 having an atraumatic tip 108 at its distal end. The tip 108 has a proximal surface 110 which engages the distal ends of the second set of penetrating elements 104. The elements 102 and 104 interdigitate so that they can pass by each other as the first set of elements 102 is advanced distally by a pusher-tube 112. Moreover, each set of elements defines a cam surface (not shown) so that both sets will be deflected radially outwardly as the first set of elements 102 is advanced distally, as shown in FIG. 11D.

Figure 12C:
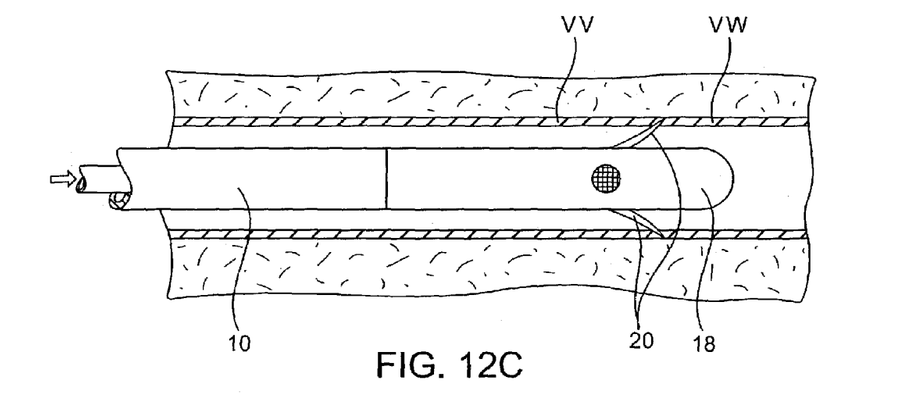

Once it is confirmed that the apparatus 10 is properly located, the penetrating elements 20 will be deployed radially outwardly to engage the inner surface of the vessel wall (VW). Optionally, proper engagement of the penetrating elements 20 can be confirmed by imaging techniques, such as fluoroscopy or duplex ultrasound.

Figure 12D:
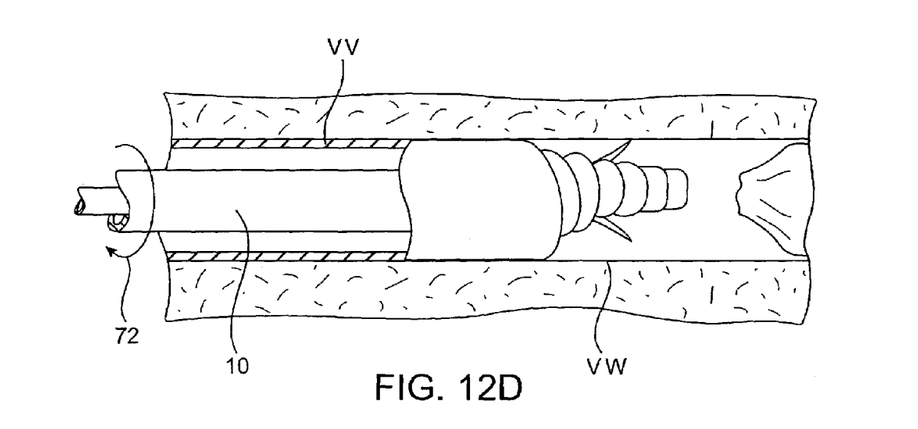

After it is confirmed that the penetrating elements 20 have properly engaged the vessel wall (VW), the apparatus 10 is rotated about its axis, as indicated by arrow 72 in FIG. 12D. Such rotation pulls the vessel wall radially inwardly and away from the surrounding connective tissue. Usually, capture and rotation of the vein will be sufficient to both tear the vein from the surrounding connective tissue and separate the vein from the remaining portions of the vein which are not being removed. In some instances, however, it might be desirable to perform a separate step of severing the venous wall, either via a percutaneous approach or using an endoluminal tool (not illustrated) which could use a blade or other severing device in order to perform the desired step. It is a particular benefit of the present invention, however, that such separate severing step is usually not needed.

After a distal portion or segment of the vessel wall VW has been drawn down to the outside of the apparatus 10 shaft, as shown in FIG. 12D, the vessel could be removed by continued rotation of the apparatus to draw down additional vessel wall, typically at least one-half of the length of the target segment to be removed, and optionally additional length up to and including the entire length of the vessel wall to be removed. At any point, of course, it would be possible to stop rotation of the apparatus and retract the apparatus proximally in order to avulse at least a portion of the vessel wall. In some instances, however, retraction of the apparatus proximally will result in collapse or "accordianing" of the vessel wall as it is withdrawn. Often, when either rotating the vessel or collapsing the vessel, the vessel will break at a point intermediate within the length to be removed. The broken segment or length may then be withdrawn and the device reintroduced to the vessel in order to capture a distal end of the remaining length and withdraw the remaining length and withdraw the remaining length (or a portion or segment thereof) from the lumen. The steps of introducing the apparatus, capturing a distal end of the vessel, and removing the vessel may be repeated as many times as necessary in order to remove the entire target length of the vessel.

In other instances, prior to removal of the vein, it may be desirable to disrupt the attachment of the vein to surrounding connective tissue, either by mechanical dissection techniques and/or through the use of tumescent anesthesia fluid infiltration. In order to assist in capture of the vein by the penetrating elements, it may be desirable to externally compress the capture site. That is, by applying manual external compression at the site (which may be observed using the light signal described previously), the ability of the penetrating elements to penetrate and capture the vessel wall may be enhanced.

Figure 12E:
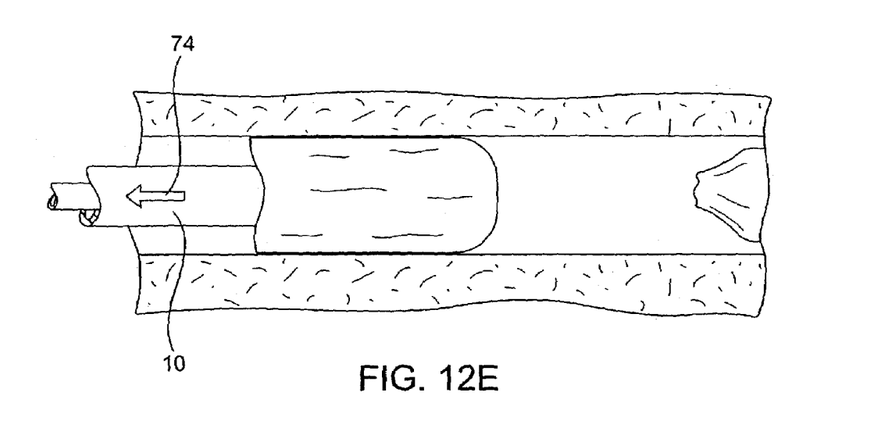

Once the capture step has been successfully completed, and the vein separated from remaining portions thereof, the apparatus 10 may be drawn proximally, as shown by arrow 74 in FIG. 12E. Drawing the apparatus 10 in this direction pulls the vessel wall (VW) proximally, avulsing and everting the wall as it is pulled away and separated from the surrounding connecting tissue, as shown in FIG. 12E. Optionally, the apparatus 10 may be continuously or periodically rotated about its axis as it is being drawn proximately. Such further rotation can facilitate vein avulsion, making it less traumatic for the patient. The rotation also maintains the torsional load on the devise and penetrating elements so that vessel engagement is maintained.

Figure 12F:
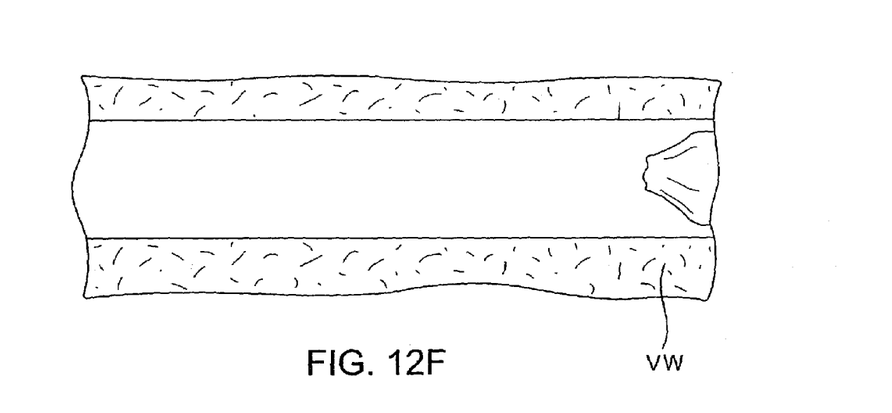

After the device 10 is withdrawn completely from the original axis penetration, the vessel can be severed and the remaining end closed by conventional surgical techniques or simply allowed to heal without further intervention. The vessel wall will have been completely withdrawn from the surrounding connective tissue, as shown in FIG. 12F. The procedure can be repeated for additional lengths of the same varicose vein or for different varicose veins, as desired.

What is claimed is:

1. A method for removing a blood vessel having a vessel wall from tissue, said method comprising:
   introducing a shaft having retracted penetrating elements into a lumen of the vessel at a proximal location;
   advancing a distal end of the shaft to a distal location within the vessel lumen; exposing the penetrating elements and capturing the vessel wall at the distal location within the lumen with the distal end of the shaft; and
   manipulating the shaft to remove the vessel from the tissue while the vessel wall remains captured by the penetrating elements;
   wherein exposing and capturing comprise advancing at least one penetrating element from the shaft into the vessel wall and rotating the shaft to separate the vessel wall from surrounding tissue;
   wherein the at least one penetrating element is deformable and advancing comprises advancing the element over a ramp which deflects the element radially outwardly.

2. A method as in claim 1, wherein capturing the vessel wall is effected without external tissue penetration in the region of the distal location.

3. A method as in claim 1, further comprising intraluminally generating a signal at the distal location and externally observing the signal to confirm the position of the shaft distal end prior to exposing the penetrating elements and capturing the vessel.

4. A method as in claim 1, wherein the at least one penetrating element is resilient and preshaped to diverge radially outwardly as the element is advanced from the shaft.

5. A method as in claim 1, wherein the introducing is performed while the penetrating elements are retracted toward a longitudinal axis of the shaft, and the exposing is performed by extending the penetrating elements away from the longitudinal axis.

6. A method as in claim 1, wherein manipulating the shaft comprises retracting the shaft proximally to invaginate the vessel.

7. A method as in claim 1, wherein manipulation of the shaft comprises rotating the shaft to draw down at least a distal portion of the vessel onto the shaft.

8. A method as in claim 1, further comprising severing the vessel at the distal location prior to retracting the shaft.

9. A method as in claim 1, further comprising disrupting the connective tissue mechanically or by introduction of tumescent anesthesia prior to shaft retraction.

10. A method as in claim 1, further comprising applying manual pressure over the distal location to facilitate penetration of the vessel wall by the at least one penetrating element.

11. A method as in claim 1, further comprising severing the vessel wall at the proximal location after the shaft has been retracted back to the proximal location.

* * * * *